United States Patent
Douglas et al.

(10) Patent No.: US 6,893,394 B2
(45) Date of Patent: May 17, 2005

(54) ILLUMINATED AND VACUUM ASSISTED RETRACTOR

(75) Inventors: Peter Douglas, New Milford, NJ (US); Daniel Gordon, Newtown, PA (US)

(73) Assignee: Ethicon, Inc., Somerville, NJ (US)

( * ) Notice: Subject to any disclaimer, the term of this patent is extended or adjusted under 35 U.S.C. 154(b) by 33 days.

(21) Appl. No.: 10/323,540

(22) Filed: Dec. 19, 2002

(65) Prior Publication Data

US 2004/0122293 A1 Jun. 24, 2004

(51) Int. Cl.[7] .................................. A61B 1/32
(52) U.S. Cl. .................. 600/205; 600/208; 600/212; 600/213
(58) Field of Search ....................... 600/205, 208, 600/212, 213

(56) References Cited

U.S. PATENT DOCUMENTS

| | | | |
|---|---|---|---|
| 3,638,644 A * | 2/1972 | Reick .................... | 600/191 |
| 3,641,332 A * | 2/1972 | Reick et al. ............. | 362/582 |
| 3,768,477 A * | 10/1973 | Anders et al. ............ | 433/91 |
| 4,562,832 A * | 1/1986 | Wilder et al. ............ | 600/223 |
| 5,005,108 A | 4/1991 | Pristash et al. | |
| 5,452,733 A | 9/1995 | Sterman et al. | |
| 5,520,611 A | 5/1996 | Rao et al. | |
| 5,571,215 A | 11/1996 | Sterman et al. | |
| 5,613,751 A | 3/1997 | Parker et al. | |
| 5,613,937 A | 3/1997 | Garrison et al. | |
| 5,618,096 A | 4/1997 | Parker et al. | |
| 6,176,824 B1 * | 1/2001 | Davis ..................... | 600/178 |
| 6,193,652 B1 * | 2/2001 | Berky et al. ............. | 600/205 |
| 6,241,658 B1 * | 6/2001 | Goodrich ................ | 600/210 |
| 6,478,728 B1 * | 11/2002 | Wright ................... | 600/37 |
| 2003/0060685 A1 * | 3/2003 | Houser et al. ........... | 600/206 |
| 2003/0095781 A1 * | 5/2003 | Williams ................ | 385/146 |

* cited by examiner

Primary Examiner—Pedro Philogene
Assistant Examiner—David A Bonderer

(57) ABSTRACT

A retractor including: an extension member having distal and proximal ends; a retractor member connected to the distal end of the extension member, the retractor member having a retractor surface. In a first implementation, at least a portion of the retractor surface has a distal vacuum port for positively retaining the tissue upon application of a vacuum to the vacuum port. In an alternative implementation, the retractor has an illuminator for transmitting light into an interior of the body proximate to the tissue.

20 Claims, 3 Drawing Sheets

ILLUMINATED AND VACUUM ASSISTED RETRACTOR

BACKGROUND OF THE INVENTION

1. Field of the Invention

The present invention relates generally to retractors for retracting tissue, and more particularly, to an atrial retractor for use in retracting the heart wall during minimally invasive heart valve surgery.

2. Prior Art

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic cross clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest to the present invention are intracardiac procedures for surgical treatment of heart valves, especially the mitral and aortic valves. Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced, by excising the valve leaflets of the natural valve, and securing a replacement valve in the valve position, usually by suturing the replacement valve to the natural valve annulus. Various types of replacement valves are in current use, including mechanical and biological prostheses, homografts, and allografts.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position accessible through the sternotomy. An opening, or atriotomy, is then made in the right side of the left atrium, anterior to the right pulmonary veins. The atriotomy is retracted by means of sutures or retraction devices, exposing the mitral valve directly posterior to the atriotomy. One of the aforementioned techniques may then be used to repair or replace the valve.

An alternative technique for mitral valve access may be used when a median sternotomy and/or rotational manipulation of the heart are undesirable. In this technique, a large incision is made in the right lateral side of the chest, usually in the region of the fourth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy which enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

In response to the various problems associated with open-chest procedures, new methods of performing closed-chest surgery on the heart using minimally invasive thoracoscopic techniques have been recently developed. In these methods, the patient's heart is arrested by occluding the patient's aorta between the coronary arteries and the brachiocephalic artery with an expandable balloon on the distal end of an endovascular catheter introduced via a femoral artery. Cardioplegic fluid is then delivered to the patient's myocardium through a lumen in the same catheter or through a catheter positioned in the coronary sinus via a peripheral vein. To repair or replace the mitral valve, minimally-invasive cutting and suturing instruments are then introduced thoracoscopically through a trocar sleeve in the right lateral portion f the chest. A complete description of such methods is found in U.S. Pat. No. 5,571,215 to Sterman, et al., issued on Nov. 5, 1996, the contents of which is incorporated herein by reference.

This new generation of thoracoscopic methods of performing heart valve repair has, of course, created many new challenges. One such challenge is that of retracting the left atrial wall to open the atriotomy so that the mitral valve can be exposed for the surgical procedure. The heart wall must be retracted anteriorly to suitably expose the mitral valve and provide access through the atriotomy for the cutting and suturing instruments introduced through the right lateral portion of the chest. In addition, the instruments that retract the heart wall must be introduced in a minimally-invasive manner through small percutaneous incisions or cannulae positioned in intercostal spaces in the patient's rib cage.

Introducing an instrument through an intercostal space in the anterior side of the chest presents additional problems.

One such problem is that the patient's rib cage is typically structured so that the ribs in the anterior portion of the chest are closer together than in the lateral portions of the chest. In addition, the tissue layer in the anterior chest wall contains nerves that could be damaged by a large percutaneous incision. Therefore, a retraction device introduced from the anterior side should be as small as possible, preferably on the order of 3–8 mm, to fit within the smaller anterior intercostal spaces and to avoid unnecessary trauma to the patient. Another problem is that the part of the retraction device that engages the heart wall must be wide enough to engage a sufficient portion of the heart wall to open the atriotomy enough to expose the mitral valve. It must also be long enough to extend a sufficient distance into the heart to extend beneath the interatrial septum and prevent it from sagging or otherwise inhibiting access to the mitral valve. Introducing an instrument that is large enough to sufficiently expose the mitral valve through the smaller intercostal spaces in the anterior portion of the chest is problematic.

U.S. Pat. No. 5,613,937 to Garrison, et al., issued on Mar. 25, 1997, the contents of which are incorporated herein by reference, teaches such an instrument. The retractor of U.S. Pat. No. 5,613,937 includes a threaded shaft and a retractor blade having a mating threaded portion. The retractor blade has a width and length sufficient to provide the necessary retraction of the heart wall and has a thickness that allows it to pass through a lateral thoracotomy. Therefore, the retractor blade and threaded shaft are disassembled and the retractor blade is positioned in the chest cavity. Once inside the chest cavity, the thin threaded shaft is also passed through the intercostal space and is mated to the retractor blade. The retractor is then used to retract the left atrial wall to open the atriotomy so that the mitral valve can be exposed for the surgical procedure. Generally, in these types of retractors, surface texturing or raised projections are provided to keep the heart wall from slipping off of the retractor blade. Since the retractors of the prior art use mechanical force applied to the retractor to hold the atrium open, it may cause the heart wall to compress over time, which causes trauma and the need to adjust the retractor to compensate for the compression. Also due to the inherent force needed to lift the heart wall, the chest wall (which supports the retractor) may be pulled down toward the heart instead of the heart wall being lifted. Furthermore, when such retractors are used to provide access to the mitral valve, illumination devices must also be used to illuminate the interior of the heart so that the surgeon can see the valve and perform the necessary procedures. Typically, the illumination device is an endoscope having a light fiber attached to a light source or a light source adapted to the surgeon's head, such as on his glasses or forehead. Therefore, illumination of the interior of the heart requires additional instrumentation and because it is external to the heart interior, it often produces shadows and dark regions, which make it difficult for the surgeon to visualize valves in the heart's interior.

SUMMARY OF THE INVENTION

Therefore it is an object of the present invention to provide a retractor that overcomes the disadvantages associated with retractors of the prior art.

Accordingly, a first implementation of a retractor is provided. The first implementation retractor comprises: an extension member having distal and proximal ends; a retractor member connected to the distal end of the extension member, the retractor member having a retractor surface, at least a portion of the retractor surface having a distal vacuum port for positively retaining tissue upon application of a vacuum to the vacuum port.

Preferably, the extension member is a tubular member having an internal lumen extending from the proximal end to the distal end. The retractor member preferably has an internal conduit in fluid cooperation with both the internal lumen and distal vacuum port, wherein vacuum applied to the proximal end of the extension member is applied to the distal vacuum port through the internal lumen and internal conduit. The retractor preferably further comprising a handle disposed at the proximal end of the extension member, the handle having a proximal vacuum port in fluid communication with the proximal end of the internal lumen. Preferably, the distal end of the extension member has a male threaded portion and the retractor member has a female threaded portion threadingly engaging the male threaded portion of the extension member.

Preferably, the retractor member is a curved blade, the curved blade having a convex surface and a concave surface, wherein the distal vacuum port is at least partially formed in the convex surface. The convex surface preferably further has at least one lip for preventing the tissue from slipping from the retractor surface.

The retractor preferably further comprises illumination means for transmitting light into an interior of the body proximate to the tissue. Preferably, the illumination means comprises the retractor member having at least a portion fabricated from a light transmitting material and light guide means for directing the light to the light transmitting material. The extension member is preferably a tubular member having an internal lumen extending from the proximal end to the distal end, wherein a light fiber is disposed in the internal lumen for directing the light to the light transmitting material. The retractor member is preferably a curved blade, the curved blade having a convex surface and a concave surface, wherein the distal vacuum port is formed at least partially on the convex surface and the light transmitting material is at least partially formed in the concave surface.

Also provided is a second implementation retractor. The second implementation comprises: an extension member having a distal and proximal end; a retractor member connected to the distal end of the extension member, the retractor member having a retractor surface and is configured as a curved blade, the curved blade having a convex surface and a concave surface; and illumination means for transmitting light into an interior of the body proximate to tissue being retracted, wherein the illumination means transmits light from the concave surface.

Preferably, at least a portion of the retractor surface has a distal vacuum port for positively retaining the tissue upon application of a vacuum to the vacuum port. The extension member is preferably a tubular member having an internal lumen extending from the proximal end to the distal end. Preferably, the retractor member has an internal conduit in fluid cooperation with both the internal lumen and distal vacuum port, wherein vacuum applied to the proximal end of the extension member is applied to the distal vacuum port through the internal lumen and internal conduit.

Preferably, the distal vacuum port is at least partially formed in the convex surface. Preferably, the convex surface further has at least one lip for preventing the tissue from slipping from the retractor surface. Preferably, the distal end of the extension member has a male threaded portion and the retractor member has a female threaded portion corresponding and threadingly engaging the male threaded portion of the extension member.

The illumination means preferably comprises the retractor member having at least a portion fabricated from a light transmitting material and light guide means for directing the light to the light transmitting material. Preferably, the extension member is a tubular member having an internal lumen extending from the proximal end to the distal end, wherein a light fiber is disposed in the internal lumen for directing the light to the light transmitting material. The retractor preferably further comprises a handle disposed at the proximal end of the extension member, the handle having a light guide connector in optical communication with the light fiber in the internal lumen. Preferably, the retractor member is a curved blade, the curved blade having a convex surface and a concave surface, wherein the distal vacuum port is formed at least partially on the convex surface and the light transmitting material is at least partially formed in the concave surface.

Still provided is a first implementation of a method for retracting tissue for accessing a surgical site within a body of a patient, the method comprising: engaging a surface of a retractor with the tissue to be retracted; and providing a vacuum at the surface to positively hold the tissue on the retractor surface. The method preferably further comprises directing light from the retractor to illuminate a body cavity proximate to the retractor.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Figure 1:
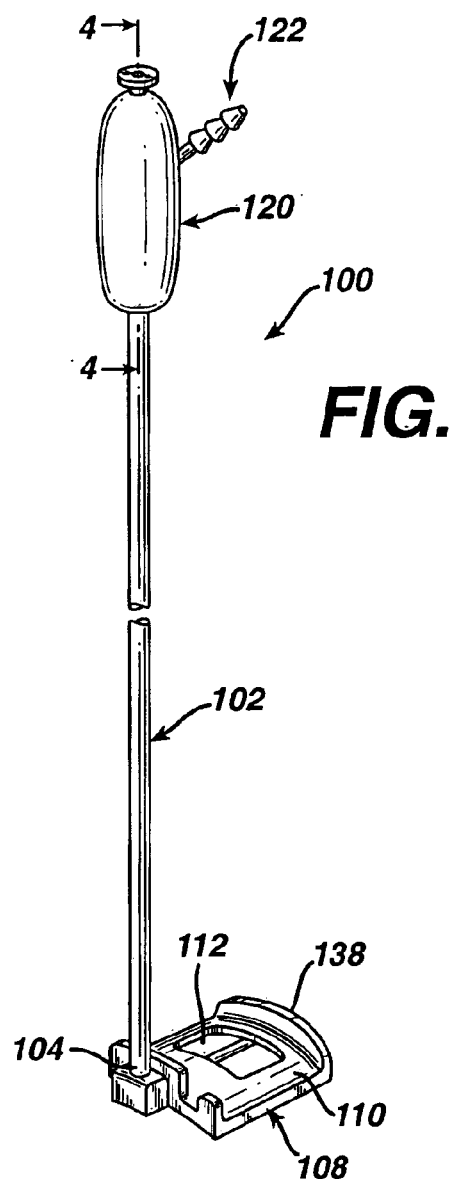
FIG. 1 illustrates an isometric view of a preferred implementation of a retractor of the present invention.

Although this invention is applicable to numerous and various types of retractors for use with retraction of different tissue, it has been found particularly useful in the environment of an atrial retractor for use in the retraction of the heart wall during minimally invasive heart valve surgery. Therefore, without limiting the applicability of the invention to an atrial retractor for use in the retraction of the heart wall during minimally invasive heart valve surgery, the invention will be described in such environment.

The invention provides methods and devices for performing surgical interventions within the heart or a great vessel such as the aorta, superior vena cava, inferior vena cava, pulmonary artery, pulmonary vein, among other vessels. While the specific embodiments of the invention described herein will refer to mitral valve repair and replacement, it should be understood that the invention will be useful in performing a great variety of surgical procedures, including repair and replacement of aortic, tricuspid, or pulmonary valves, repair of atrial and ventricular septal defects, pulmonary thrombectomy, removal of atrial myxoma, patent foramen ovale closure, treatment of aneurysms, electrophysiological mapping and ablation of the myocardium, myocardial drilling, annloplasty, artial fibulation, correction of congenital defects, and other procedures in which interventional devices are introduced into the interior of the heart, coronary arteries, or great vessels. Advantageously, the invention facilitates the performance of such procedures through percutaneous penetrations within intercostal spaces of the rib cage, obviating the need for a median sternotomy or other form of gross thoracotomy.

The terms "percutaneous intercostal penetration" and "intercostal penetration" as used herein refer to a penetration, in the form or a small cut, incision, hole, cannula, trocar sleeve, or the like, through the chest wall between two adjacent ribs, wherein the patient's rib cage and sternum remain substantially intact, without cutting, removing, or significantly displacing the ribs or sternum. These terms are intended to distinguish a gross thoracotomy such as a median sternotomy, wherein the sternum and/or one or more ribs are cut or removed from the rib cage, or one or more ribs are retracted signficantly, to create a large opening into the thoracic cavity. A "percutaneous intercostal penetration" may abut or overlap the adjacent ribs between which it is formed, but the maximum width of the penetration which is available for introduction of instruments, prostheses and the like into the thoracic cavity will be the width of the intercostal space, bounded by two adjacent ribs in their natural, substantially un-deflected positions. It should be understood that one or more ribs may be retracted or deflected a small amount without departing from the scope of the invention; however, the invention specifically seeks to avoid the pain, trauma, and complications which result from the large deflection or cutting of the ribs in conventional, open-chest techniques.

Referring now to FIG. 1, there is shown a preferred implementation of a retractor of the present invention, generally referred to by reference numeral 100. In general, the retractor 100 includes an extension member 102 having distal 104 and proximal 106 ends. A retractor member 108 is connected to the distal end 104 of the extension member 102. The retractor member 108 has a retractor surface 110 in contact with a tissue to be retracted. At least a portion of the retractor surface 110 has a distal vacuum port 112 for positively retaining the tissue upon application of a vacuum to the distal vacuum port 112.

Figure 2:
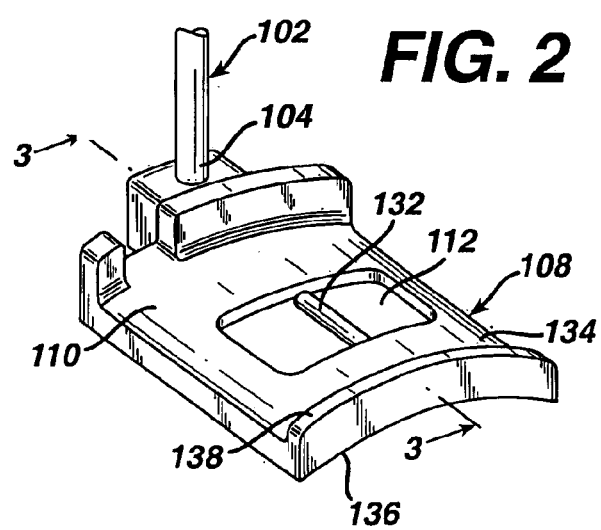
FIG. 2 illustrates a partial isometric view of the retractor member and extension member of FIG. 1.
Figure 3:
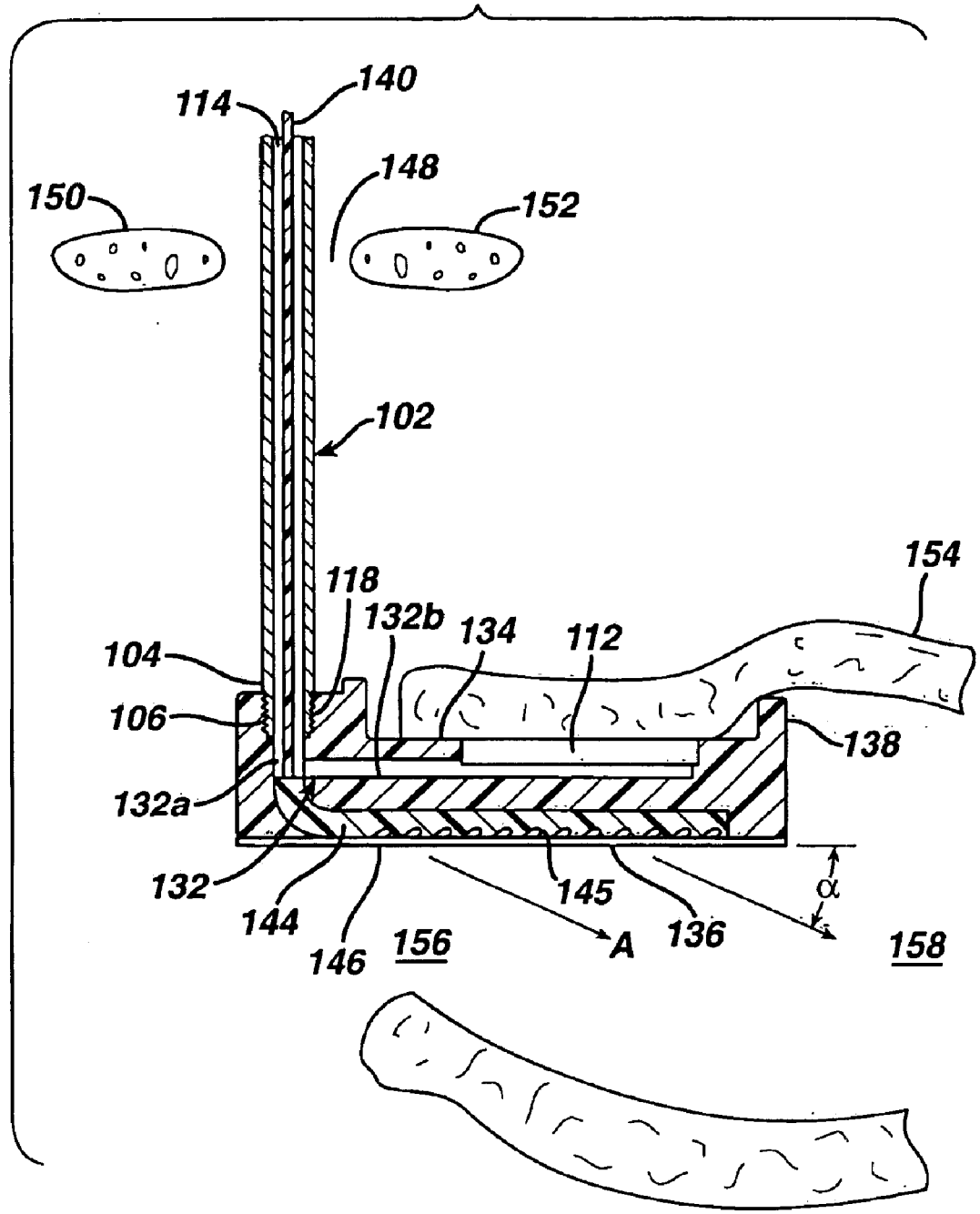
FIG. 3 illustrates a sectional view of the retractor member and extension member of FIG. 2 as taken along line 3—3 in FIG. 2, the retractor member being shown in cooperation with heart tissue and the extension member being shown disposed in an intercostal space between adjacent ribs.
Figure 4:
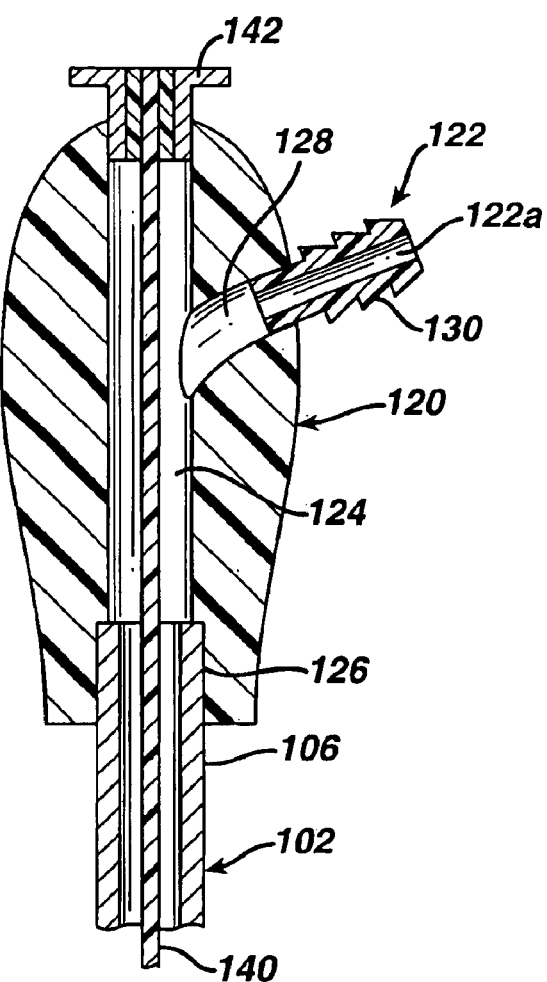
FIG. 4 illustrates a partial sectional view of the handle and extension member of the retractor of FIG. 1 as taken along line 4—4 in FIG. 1.

Referring now also to FIGS. 2, 3, and 4 the preferred implementation of the retractor 100 will be described in more detail. Preferably, the extension member 102 is a tubular member having an internal lumen 114 extending from the proximal end 106 to the distal end 104. Preferably, the extension member 102 is fabricated from surgical grade stainless steel. The distal end 104 of the extension member 102 has a means for coupling and uncoupling it with the retractor member 108. Preferably, such means is provided by a male threaded portion 116 at the distal end 104 of the extension member 102. In which case, the retractor member 108 has a corresponding female threaded portion 118 threadingly engaging the male threaded portion 116 of the extension member 102. Those skilled in the art will appreciate that other means for coupling and uncoupling the extension and retractor members 102, 108 are possible without departing from the scope or spirit of the prior art, such as a "bayonet" type means in which one or more projections (not shown) on the distal end 104 of the extension member 102, engage a spiral slot (not shown) in the retractor member 108. The bayonet type means can also have a spring or other biasing means (not shown) for biasing the projections into a locked position in the slot. Other means include a "quick-connect" type of coupling as is known in the art. Furthermore, it is preferred that the extension member 102 be used with many different size retractor members for different surgical applications. Each of the different size retractor members 108 are interchangeably coupled and uncoupled from the extension member 102.

Preferably, a handle 120 is disposed at the proximal end 106 of the extension member 102. As well as providing a convenient place for a surgeon to grasp and manipulate the retractor 100, the handle 120 also has a proximal vacuum port 122 in fluid communication with the proximal end 106 of the internal lumen 114. The handle 120 has a main bore 124, a distal portion of which preferably has a counter bore 126 which is press fit and/or adhered with an adhesive to the proximal end 106 of the extension member 102. Those skilled in the art will appreciate that other means of fastening the handle to the extension member are possible without departing from the scope or spirit of the present invention, such as a threaded connection similar to that described with regard to the distal end 104 of the extension member 102. The proximal vacuum port 122 is preferably a barbed fitting 122 as is known in the art. The barbed fitting is also preferably press fit and/or adhered with an adhesive into a side bore 128 which is in fluid communication with the main bore 124. The barbed fitting has an internal conduit 122a and one or more external barbs 130 over which flexible tubing is sealingly disposed. The flexible tubing (not shown) is attached to a vacuum source (not shown) such as a vacuum pump (not shown) for generating a vacuum at the proximal vacuum port 122. Other types of vacuum fittings are also possible, such as luer fittings known in the medical arts. Furthermore, a syringe (not shown) may be connected directly to the flexible tubing for applying a vacuum at the proximal vacuum port 122.

Figure 5:
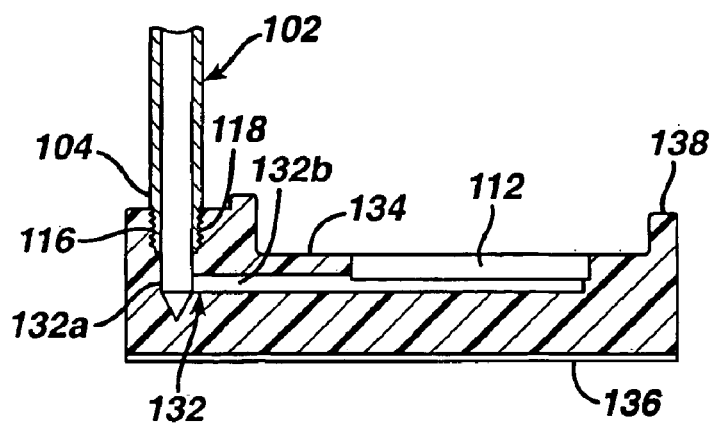
FIG. 5 illustrates a sectional view of an alternative implementation of the retractor member and extension member of FIG. 2 as if it were taken along line 3—3 in FIG. 2.

The retractor member 108 preferably has an internal conduit 132 in fluid cooperation with both the internal lumen 114 of the extension member 102 and the distal vacuum port 112. The internal conduit 132 preferably comprises two segments, a first segment 132a, which is a continuation of the female thread 118, and a second segment 132b that connects the first segment 132a to the distal vacuum port 112. The distal vacuum port 112 is preferably shaped to cover a major portion of the retractor surface 110, such as a rectangle. Those skilled in the art will appreciate that other shapes or several shapes and ports are possible without departing from the scope or spirit of the present invention. From the foregoing description, those skilled in the art will also appreciate that vacuum applied to the proximal end of the extension member is applied to the distal vacuum port 112 through the internal lumen 114 and internal conduit 132. Where the handle 120 is provided, the vacuum applied at the proximal vacuum port 122 is applied to the distal vacuum port 112 through the conduit 122a, side bore 128, main bore 124, internal lumen 114 and internal conduit 132. Those skilled in the art will appreciate that the vacuum path to the distal vacuum port 112 may vary from that described above with regard to the preferred implementation of the retractor 100. For example, a vacuum port may be provided directly on a surface of the retractor member 108 and a flexible tube connected thereto and to a vacuum source can be external to the extension member 102. As discussed below, the retractor member 108 is preferably fabricated from a transparent material, at least a portion of which is fabricated from a light transmitting material, to facilitate illuminating an interior of the body proximate the retractor member 108. However, as shown in FIG. 5, the retractor 100 may be configured without such an illumination means, and as such, may be fabricated from any appropriate medically approved material, such as a thermoplastic, or stainless steel.

The retractor surface 110 of the retractor member 108 is configured to retract tissue, preferably, heart tissue. Preferably, the retractor member 108 is shaped as a curved rigid blade wherein the retractor surface 10 is a convex surface 134 and the retractor member 108 further has a concave surface 136. The distal vacuum port 112 is preferably at least partially formed in the convex surface 134 corresponding to the retractor surface 110. The convex surface 134 further has at least one lip 138 for preventing the tissue from slipping from the retractor surface 110. Although, suction generated at the distal vacuum port 112 may act to positively retain the tissue on the retractor surface 110, the lip 138 provides additional retention of the tissue and may serve to retain the tissue while the retractor 100 is being positioned and before the vacuum is applied or fully established.

As discussed briefly above, the retractor 100 preferably further comprises illumination means for transmitting light into an interior of the body proximate to the tissue. The illumination means preferably comprises the retractor member 108 having at least a portion fabricated from a light transmitting material and light guide means for directing the light to the light transmitting material. In the preferred implementation of the retractor 100 discussed above where the extension member 102 is a tubular member having an internal lumen 114, a light fiber 140 is disposed in the internal lumen 114 for directing the light to the light transmitting material. Where suction is also provided at the retractor surface 110, the vacuum is applied through an annular space between the exterior surface of the light fiber 140 and an interior surface of the internal lumen 114. Furthermore, the handle 120 includes a light guide coupling 142 for coupling a light guide cable (not shown) from a light source (not shown) to the light fiber 140. Light guide couplings 142 for coupling light sources to internal light fibers 142 or optics are well known in the medical arts, particularly in the endoscope arts.

Preferably, the retractor member 108 is fabricated from a transparent material and has a light pipe 144 molded therein. The light pipe 144 is fabricated from a light transmitting material, such as polycarbonate. The light fiber 140 directs light onto a surface of the light pipe 144, which directs the light as desired. Where, the retractor member 108 is a curved blade as discussed above, having a convex surface 134 and a concave surface 136, the light transmitting material, e.g., the light pipe 144, is at least partially formed in the concave surface 136 to direct the light from the concave surface 136. Preferably, small lenses 145, such as Microlens® manufactured by Lumitex Inc., are molded into the concave surface 136 in the vicinity of the light pipe 144 to direct the light A from the concave surface 136 at a predetermined angle α with respect to the concave surface 136. In this way, light is diffusely delivered into an operative area through the retractor member 108. The predetermined angle a can be chosen depending on the application for the retractor 100. When used in mitral valve repair or replacement, the preferred angle α is approximately 30 degrees. When using the small lenses 145 molded in the concave surface 136, it is preferred that an additional layer 146 is disposed on the concave surface 136. The additional layer 146 can be molded onto the retractor member 108 as a secondary operation to the fabrication of the retractor member 108. However, it is preferred that the additional layer be a thin transparent adhesive label that is adhered to the concave surface 136.

In addition to performing mitral valve repair and replacement, the techniques of the invention also facilitate surgical intervention into other regions of the heart and great vessels and may also be used in other vessels and organs in general. The devices and methods described above may be used to form an opening directly into the left ventricle, right atrium, or right ventricle, or into a great vessel such as the aorta, superior vena cava, inferior vena cava, pulmonary artery, or pulmonary vein, for surgical intervention in such cavities. For example, a penetration may be made in the wall of the aorta, and the aortic valve may be repaired or replaced with prosthesis, using techniques and devices like those described above for mitral valve replacement. Moreover, the devices and methods of the invention also facilitate intercardiac procedures such as repair of atrial or ventricular septal defects, electrophysiological mapping and ablation of the myocardium, myocardial drilling, and other procedures. Furthermore, devices may be introduced through an opening into the heart or great vessel and advanced therefrom into vessels such as the coronary arteries to perform procedures such as angioplasty, atherectomy, coronary artery bypass grafting, or treatment of aneurysms. The retractor 100 is preferably used in combination with a thoracotomy or sternotomy retractor or used as a stand-alone retractor system that uses the patient's chest wall as its opposing force. Preferably, the retractor 100 is fastened to the thoracotomy or sternotomy retractor by using a ball socket clamp as is known in the art. The ball socket clamp preferably grasps the retractor 100 by the extension member 102.

EXAMPLE

An example procedure using the preferred implementation retractor 100 of the present invention for minimally invasive mitral valve surgery will now be described with reference to FIGS. 3 and 4. The extension member 102 with light fiber 140 is inserted first using a stab incision through an intercostals space 148 on the patients chest between adjacent ribs 150, 152. The retractor member 108 is then inserted into the operative space through a lateral thoracotomy and is threaded onto the distal end 104 of the extension member 102. Once the extension member 102 is attached to the retractor member 108, a light source (not shown) and vacuum line (not shown) are attached to the light guide coupling 142 and proximal vacuum port 122, respectively. The connection of the light fiber to the retractor member 108 is inherently made when the extension member 102 is connected to the retractor member 108. The retractor member 108 is then positioned in the right atrium of the heart 154 through an atriotomy 156. Once the retractor 100 is in place, the suction is turned on to hold the position of the retractor member 108 relative to the heart 154. The extension member 102 is then attached to a thoracotomy retractor (not shown) or can be used on its own by using the patients chest for the opposing force once the atrium wall is lifted. The latter would be done by using a clamp around the extension member 102 or an assisting device such as an "Atrial Assistant" manufactured by Heartport Inc. Once the retractor 100 is anchored, the light source (not shown) is turned on to illuminate the interior 158 of the heart 154 including the atrium and the mitral valves. The physician then repairs of replaces the atrium and/or mitral valves as discussed above and as is known in the art.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A retractor comprising:
    an extension member having distal and proximal ends;
    a retractor member connected to the distal end of the extension member, the retractor member having an upper and lower retractor surface, at least a portion of the upper retractor surface having a distal vacuum port for positively retaining tissue to be retracted upon application of a vacuum to the vacuum port and a lip for retaining the tissue prior to full application of the vacuum.

2. The retractor of claim 1, wherein the extension member is a tubular member having an internal lumen extending from the proximal end to the distal end.

3. The retractor of claim 2, wherein the retractor member has an internal conduit in fluid cooperation with both the internal lumen and distal vacuum port, wherein vacuum applied to the proximal end of the extension member is applied to the distal vacuum port through the internal lumen and internal conduit.

4. The retractor of claim 3, further comprising a handle disposed at the proximal end of the extension member, the handle having a proximal vacuum port in fluid communication with the proximal end of the internal lumen.

5. The retractor of claim 2, wherein the distal end of the extension member has a male threaded portion and the retractor member has a female threaded portion threadingly engaging the male threaded portion of the extension member.

6. The retractor of claim 1, wherein the retractor member is a curved blade, the curved blade having a convex surface and a concave surface, wherein the distal vacuum port is at least partially formed in the convex surface.

7. The retractor of claim 1, further comprising illumination means for transmitting light into an interior of the body proximate to the tissue.

8. The retractor of claim 7, wherein the illumination means comprises the retractor member having at least a portion fabricated from a light transmitting material and light guide means for directing the light to the light transmitting material.

9. The retractor of claim 8, wherein the extension member is a tubular member having an internal lumen extending from the proximal end to the distal end, wherein a light fiber as disposed in the internal lumen for directing the light to the light transmitting material.

10. The retractor of claim 9, wherein the retractor member is a curved blade, the curved blade having a convex surface and a concave surface, wherein the distal vacuum port is formed at least partially on the convex surface and the light transmitting material is at least partially formed in the concave surface.

11. A retractor comprising:
    an extension member having a distal and proximal end;
    a retractor member connected to the distal end of the extension member and having a retractor surface configured as a curved blade, the curved blade having an upper convex surface and a lower concave surface wherein at least a portion of the retractor surface has a distal vacuum port for positively retaining tissue upon application of a vacuum to the vacuum port;

a lip on at least a portion of the upper convex surface for retaining the tissue to be retracted; and illumination means for transmitting light into an interior of the body proximate to the tissue being retracted, wherein the illumination means transmits light from the lower concave surface.

12. The retractor of claim 11, wherein the extension member is a tubular member having an internal lumen extending from the proximal end to the distal end.

13. The retractor of claim 12, wherein the retractor member has an internal conduit in fluid cooperation with both the internal lumen and distal vacuum port, wherein vacuum applied to the proximal end of the extension member is applied to the distal vacuum port through the internal lumen and internal conduit.

14. The refractor of claim 11, wherein the distal vacuum port is at least partially formed in the convex surface.

15. The retractor of claim 11, wherein the distal end of the extension member has a male threaded portion and the retractor member has a female threaded portion corresponding and threadingly engaging the male threaded portion of the extension member.

16. The retractor of claim 11, wherein the illumination means comprises the retractor member having at least a portion fabricated from a light transmitting material and light guide means for directing the light to the light transmitting material.

17. The retractor of claim 16, wherein die extension member is a tubular member having an internal lumen extending from the proximal end to the distal end, wherein a light fiber is disposed in the internal lumen for directing the light to the light transmitting material.

18. The retractor of claim 17, further comprising a handle disposed at the proximal end of the extension member, the handle having alight guide connector in optical communication with the light fiber in the internal lumen.

19. A method for retracting tissue for accessing a surgical site within a body of a patient, the method comprising:

engaging an upper surface of a retractor with the tissue to be retracted;

retaining the tissue to be retracted on the upper surface of the retractor using a lip projecting upward from the surface of the retractor; and providing a vacuum at the upper surface to positively hold the tissue on the retractor surface.

20. The method of claim 19, further comprising directing light from the retractor to illuminate a body cavity proximate to the retractor.

* * * * *